United States Patent [19]

Hood et al.

[11] Patent Number: 4,956,297

[45] Date of Patent: Sep. 11, 1990

[54] DEVICE FOR OBTAINING PREDETERMINED AMOUNTS OF BACTERIA

[75] Inventors: John K. Hood, St. Paul; Marlys E. Lund, Eden Prairie; Robert L. Nelson, Bloomington, all of Minn.

[73] Assignee: Minnesota Mining and Manufacturing Company, St. Paul, Minn.

[21] Appl. No.: 310,324

[22] Filed: Feb. 13, 1989

[51] Int. Cl.$^5$ ............................................. C12M 1/26
[52] U.S. Cl. .................................. 435/292; 435/294; 435/810; 422/61
[58] Field of Search .................. 435/294, 30, 295, 810, 435/292; 422/61, 100

[56] References Cited

U.S. PATENT DOCUMENTS

| | | | |
|---|---|---|---|
| 4,250,264 | 2/1981 | Nelson et al. | 435/253 |
| 4,252,904 | 2/1981 | Nelson et al. | 435/294 |
| 4,345,028 | 8/1982 | Nelson et al. | 435/30 |
| 4,657,869 | 4/1988 | Richards et al. | 435/292 |

Primary Examiner—Larry Jones
Attorney, Agent, or Firm—Donald M. Sell; Walter N. Kirn; Philip M. Goldman

[57] ABSTRACT

A wand assembly having an elongate rod with a lower end having a groove or grooves formed therein. When contacted with (e.g., touched to) a colony, the lower end is able to ingest a predetermined quantity of bacteria into the groove or grooves by capillary action. The wand assembly is particularly suitable for ingesting very small quantities of bacteria, e.g., on the order of $1 \times 10^7$ colony forming units, since it is provided with a collar that is releasably attached to the rod, and can be detached from the rod after the lower end has been touched to a colony, in a manner that wipes excess, unwanted bacteria from the peripheral surface of the rod.

8 Claims, 1 Drawing Sheet

DEVICE FOR OBTAINING PREDETERMINED AMOUNTS OF BACTERIA

TECHNICAL FIELD

Background Art

A number of microbiological procedures, such as those used to identify bacteria or determine the susceptibility of bacteria to certain antibiotics, require the ability to reproducibly and accurately obtain and deliver a predetermined amount of bacteria. A traditional approach to obtaining a predetermined amount involves a comparison of the cloudiness or turbidity of a bacterial suspension or dilution to the turbidity of one or more known standards, in order to determine the concentration of bacteria in the suspension.

In another approach, U.S. Pat. Nos. 4,252,904, 4,250,264 and 4,345,028 relate to a system for growing bacteria from a predetermined initial population to a predetermined final population. These patents relate, respectively, to a device for growing the bacteria, to growth limiting media, and to a wand for picking up a predetermined quantity of bacteria. For instance, the '028 patent describes a Minimum Inhibitory Concentration (MIC) test for determining the susceptibility of various bacteria to antibiotics.

In a commercial embodiment of such an MIC test an inoculum of $1 \times 10^8$ Colony Forming Units ("CFU") is picked up with an "inoculation wand". The inoculum is picked up by capillary action into a groove or grooves formed in the tip of the wand. The wand is then transferred to an "inoculation bottle" containing 30 ml of buffered solution. The bottle is then shaken to dislodge bacteria from the tip of the wand. In one such test, 5 microliter aliquots of the buffered solution are then added to 50 microliter nutrient solutions This series of dilutions is intended to result in a final concentration of $5 \times 10^5$ CFU/ml for purposes of the MIC test. See, e.g., "Prompt TM Inoculation System-F" product literature, Baxter Healthcare Corp., 1988.

It has become apparent however that in certain situations an inoculum much smaller than $1 \times 10^8$ would be desirable. For instance, in a variation of the MIC test format referred to above, it would be desirable to use a wand to pick up $1 \times 10^7$ rather than $1 \times 10^8$ CFU's as the initial inoculum. This inoculum could similarly be transferred to a 30 ml buffered solution, which could then be used directly to rehydrate dry nutrient medium, e.g., by using 50 microliters of the solution itself, in order to again achieve a final concentration of approximately $5 \times 10^5$ CFU/ml in the rehydrated medium.

A wand such as that described in the '028 patent could be made with a groove small enough to pick up such a small amount. With such a wand however there is an increased possiblity, particularly without very careful and proper technique, that the amount of bacteria adhering to the sides of the wand could begin to become significant compared to the amount intended to be picked up in the groove or grooves in the tip of the wand. The amount adhering to the sides could, therefore, affect reproducibility and accuracy when using such a wand. This potential problem points out the need to make wands that are able to pick up very small amounts of bacteria while lessening the possibility of error, e.g., due to amounts adhering to the sides of the wands.

SUMMARY OF THE INVENTION

The present invention provides a wand assembly for picking up a predetermined quantity of bacteria from at least one growth colony of the bacteria, said assembly comprising:

an elongate rod having an axis, opposite upper and lower ends, an upper portion adjacent the upper end adapted for manual engagement, an elongate tip portion adjacent the lower end, the tip portion having a peripheral surface and a generally uniform cross sectional shape along the axis, the tip portion having a groove opening through the lower end with the groove having a size adapted to ingest the predetermined quantity of bacteria by capillary action;

a collar around the rod, the collar comprising a wiping portion adapted to move axially in close proximity along the peripheral surface of the tip portion to wipe unwanted bacteria from the peripheral surface; and means for releasably attaching the collar to the rod at a predetermined axial distance from the lower end with the wiping portion adjacent the peripheral surface.

In a preferred embodiment of the invention the wand assembly is integrally molded of polymeric material and the means for releasably attaching is a thin layer of the polymeric material joining the wiping portion to the rod, the thin layer being adapted to be broken upon application of a moderate force to move the collar axially along the tip portion toward the lower end. The thin layer is preferably of a thickness similar to that of "flash". Flash is generally considered a flaw that is to be carefully avoided in the injection molding of plastics, such as the small flaps of plastic occassionally seen at the parting line of the mold on injected molded pieces. Applicants have found that a structure similar to flash can be deliberately created, and can be used as means for releasably attaching the wiping portion of a collar to the peripheral surface of a rod of the present invention.

DETAILED DESCRIPTION

The elongate rod of the present invention can be prepared and used in the manner described in U.S. Pat. No. 4,345,028, the disclosure of which is hereby incorporated by reference. Preferred rods are capable of picking up very small amounts of bacteria, e.g., on the order of $10^7$ CFU or less. Presumably they pick up the bacteria by capillary action, in which the bacterial colony, which is generally rather viscous, is able to rise into and fill the groove when touched with the lower end of the tip portion of the rod. In order to pick up such small amounts, the groove has a size adapted to ingest the predetermined quantity of bacteria by capillary action. Rods containing such grooves can be prepared by any suitable means, e.g., by micro-etching the tip of the rod, or forming the rod by injection molding.

Initially, the collar of the present invention is releasably attached to the rod, at a predetermined axial distance from the lower end of the rod, with the wiping portion of the collar adjacent the peripheral surface of the rod. The collar can be detached from the rod, e.g., broken or displaced, by the application of moderate force, and the collar can then be moved axially along the tip portion of the rod with the wiping means in close proximity to the peripheral surface of the tip portion. The word "detach", and inflections thereof, as used herein, refers to the separation, e.g., breaking or displacement, of the collar from the rod in order to destroy the releasable attachment of the collar to the rod, and allow the collar to be removed from the rod.

The word "attach", and inflections thereof, as used herein refers to the physical interaction between the rod and collar that maintains the collar in releasable attachment to the rod while the rod is used to pick up bacteria. Releasable attachment means can be of any suitable form, e.g., the rod and collar can be prepared as a unitary piece, or they can be prepared separately and joined together, e.g., by the use of an adhesive, by a friction fit, and so on. Preferably the rod and collar are prepared as a unitary piece, thereby inherently providing attachment means between the two. Attachment means can be of any suitable configuration, e.g., to provide continuous or discontinuous attachment of the collar to the rod.

FIGS. 1 and 2 illustrate a wand assembly wherein rod 10 has a groove 14 recessed from the peripheral surface at a predetermined axial distance from lower end 16, and the wiping portion of collar 12 has an inner surface defining a central opening in the wiping portion having a smaller cross sectional area than the cross sectional area of the tip portion. A part of the wiping portion adjacent the inner surface of the collar being positioned in the groove to provide the means for releasably attaching, the wiping portion being sufficiently flexible to be displaced from the groove and slid along the tip portion upon application of a moderate force to move the collar axially along the tip portion toward lower end 16.

FIG. 2 illustrates the embodiment of FIG. 1 wherein collar 12 is shown released from groove 14 of rod 10 and removed from rod 10 over lower end 16.

A collar of the present invention is able to wipe the peripheral portion of the rod as it is removed over the lower end. The word "wipe", and inflections thereof, as used herein refers to the ability of the collar to remove substantially all bacteria, i.e., remove sufficient numbers of bacteria from the peripheral surface of the rod as the collar itself is removed, in order to enable the groove(s) of the rod to be used in a reproducible and accurate fashion. Wiping is accomplished by maintaining the wiping portion of the rod in close proximity with the peripheral surface of the tip portion as the collar is removed from the rod. Close proximity can include, e.g., maintaining the wiping portion in physical contact with the rod, or maintaining a sufficiently small clearance (e.g., less than about 0.025 mm (0.001 in.) and preferably less that about 0.013 mm (0.0005 in.)) between the wiping portion and the rod such that substantially all unwanted bacteria are wiped from the rod.

A preferred embodiment of the wand assembly of the present invention is illustrated in FIG. 3, in which wand assembly 18 is integrally molded of polymeric material and the means for releasably attaching collar 22 to rod 19 is a thin layer of the polymeric material joining the wiping portion 20 of collar 22 to rod 19, the thin layer being adapted to be broken upon application of a moderate force to move collar 22 axially along tip portion 24 toward lower end 34.

Preferably collar 22 is attached at a predetermined distance of at least 2.54 cm (1 in.) from lower end 34, and tip portion 24 is cylindrical, having a diameter of about 0.076 cm (0.03 in.). The predetermined distance is preferably on tip portion 24 and at or near the point where upper end 32 meets tip portion 24. Preferably the predetermined distance is near such point, as illustrated, in order to facilitate the manufacture of a mold.

Also shown in FIG. 3 are upper portion 26 adjacent upper end 32 of the rod and adapted for manual engagement, and optional frusto conical portion 30 between upper portion 26 and upper end 32 adapted to engage the neck of a bottle. Upper portion 26 flares radially where it meets frusto conical portion 30 in order to provide flange 28, which serves to provide a better seal when wand assembly 18 is engaged within the neck of a bottle.

Upper portion 26 is used to pick up and touch lower end 34 of wand assembly 18 to one or more bacterial colonies. A preferred upper portion is suitably sized and configured to enable it to be grasped and held by the user, e.g., between the thumb and forefinger. In this manner lower end 34 of wand assembly 18 can be carefully touched to a bacterial colony on a culture plate in order to allow bacteria to enter groove 36.

Wand assembly 18 can then be placed in a bottle (not shown), e.g., containing sterile buffered solution wherein the bacteria can be dislodged by shaking. Flange 28 is configured to suitably cover the opening of the bottle, thereby serving to create and/or improve the seal when wand assembly 18 is inserted into a bottle.

Frusto conical portion 30 is configured to snuggly fit into the bottle so as to allow the user to shake the bottle without leaking of the solution contained therein in order to dislodge substantially all of the bacteria picked up by wand assembly 18. In a preferred embodiment, frusto conical portion 30 is tapered at an angle of approximately 2 degrees as it approaches upper portion 32, and is approximately 1.14 cm (0.45 in.) in length.

As illustrated, upper end 32 is shown as having a larger diameter than tip portion 24. The diameter of upper end 32 is not particularly critical since it is above collar 22. In a preferred embodiment upper end 32 is on the order of 0.81 cm (0.32 in.) in diameter and 1.27 cm (0.5 in.) in length. Such dimensions add overall strength and durability to wand assembly 18. In a preferred embodiment, as illustrated in FIG. 4, upper end 32 narrows at a 45 degree angle with respect to its axis as it terminates, in order to approach the diameter of tip portion 24.

The thin layer of polymeric material used to releasably attach the wiping means of the collar to the rod, in the preferred embodiment of this invention, can be formed using injection molded polymeric material by intentionally forming a slight separation, or mismatch, at the parting line between the metal pieces of the mold. See, generally, "Injection Molding, Vol. 8, pp. 102–138, Vol. 8 in Encyclopedia of Polymer Science and Engineering, 2nd ed., Mark, et al., eds., John Wiley and Sons, Inc., 1987, the disclosure of which is incorporated herein by reference.

Generally the thin layer is of a thickness less than that of the adjacent rod or collar. In this manner the layer will be weaker than the rod or collar and hence will be the first part to be manually broken.

For purposes of the preferred embodiment of the present invention the thin layer is achieved by the deliberate creation of small gaps between mold pieces. In this manner thin layers on the order of 0.008 cm to 0.013 cm (0.003 in. to 0.005 in.), and preferably on the order of 0.011 cm (0.004 in.) thick can be formed. The thin layer is preferably designed and molded such that it breaks at a point as close as possible to the rod, thereby allowing the rod to be wiped by virtue of very small clearance between the wiping portion of the collar and the rod. The break point can be made sufficiently near the rod, e.g., by tapering the mold pieces in the manner illustrated in FIG. 4, such that the thin layer narrows as it approaches the peripheral surface of the rod. When broken, the thin layer remaining on the collar forms the inner surface of the wiping portion of the collar.

Figure 4:
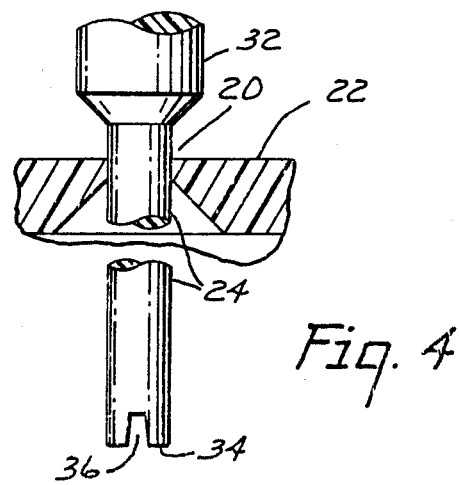
FIG. 4 is a fragmented cross-sectional view including both the wiping portion of the collar, and the lower end of the rod of FIG. 3.

At preferred dimensions as illustrated in FIG. 4, i.e., where a thin layer having a thickness on the order of 0.011 cm (0.004 in.) attaches wiping portion 22 to tip portion 24, a preferred break point is one formed by tapering the lower surface of wiping portion 22 at an angle of 45 degrees with respect to the axis of tip portion 24.

As is also seen in the preferred embodiment illustrated in FIG. 4, a single groove 36 capable of ingesting 10' bacteria can be formed in lower end 34, which is illustrated as being 0.077 cm to 0.087 cm (0.030 in. to 0.034 in.) in diameter, by molding a transverse groove across the lower end. Preferably such a groove is on the order of 0.005 cm to 0.011 cm (0.002 in. to 0.004 in.) in width at its base, and 0.018 cm to 0.020 cm (0.007 in. to 0.008 in.) wide at its opening and 0.028 cm to 0.036 cm (0.011 in. to 0.014 in.) deep.

Since wand assemblies of the present invention will frequently be used with pathogenic bacteria, preferred collars also serve the purpose of protecting the user's fingers from contact with the lower end as the wand assembly is used. In the preferred embodiment illustrated in FIG. 3 for instance, wiping portion 20 extends generally radially of rod 19 and has an outer periphery 38, and the collar further includes a generally cylindrical flange portion 40 coaxial with and spaced from the rod, the flange portion having an end attached to the outer periphery of wiping portion 22 and an opposite end projecting toward the lower end, wiping portion 22 and flange 40 defining a barrier adapted to protect a user's fingers from contact with lower end 34.

Wand assemblies of the present invention can be made, e.g., manufactured, in a variety of ways familiar to those of ordinary skill in the art, e.g., by machining, or by forming (e.g., using thermoplastic materials). Preferred wand assemblies are most conveniently and inexpensively manufactured by injection molding. Preferred injection molding parameters are described more fully in the EXAMPLES below.

Polymeric materials suitable for use in making wand assemblies of the present invention exhibit an optimal combination of such properties as elasticity, flexural strength, moldability, elongation, surface tension, tensile strength, notched izod, melt flow, and cost. Examples of suitable poylmeric materials include, but are not limited to, polystyrene, polyethylene, polypropylene, nylon, acetal, and acrylic. A preferred polymeric material is polystyrene.

Wand assemblies of the present invention can be used in a variety of ways familiar to those of ordinary skill in the art. They find their greatest applicability in situations where very small amounts of bacteria need to be picked up in a reproducible and accurate fashion, such as with MIC tests using dried substrates as described above.

In general wand assemblies of the present invention are used by;
 (a) manually engaging the upper portion and touching the lower end of the rod to the desired colony or colonies in a manner that enables the lower end to ingest the predetermined amount of bacteria in its groove(s),
 (b) detaching the collar from the rod by the application of moderate force,
 (c) axially removing the collar over the lower end, thereby causing the wiping means to remove substantially all bacteria present on the peripheral surface of the rod, and
 (d) contacting the wiped lower end to a solution or surface in a manner that transfers substantially all of the bacteria in the groove or grooves of the lower end to the solution or surface.

Both the removed collar and the remainder of the wand assembly can then be discarded in the appropriate fashion.

The invention is further illustrated by the following EXAMPLES, but the particular materials and amounts thereof recited in these EXAMPLES, as well as other conditions and details should not be construed to unduly limit this invention.

EXAMPLES

EXAMPLE 1

Manufacture of a Wand Assembly by Injection Molding

Figures 1, 2, 3:
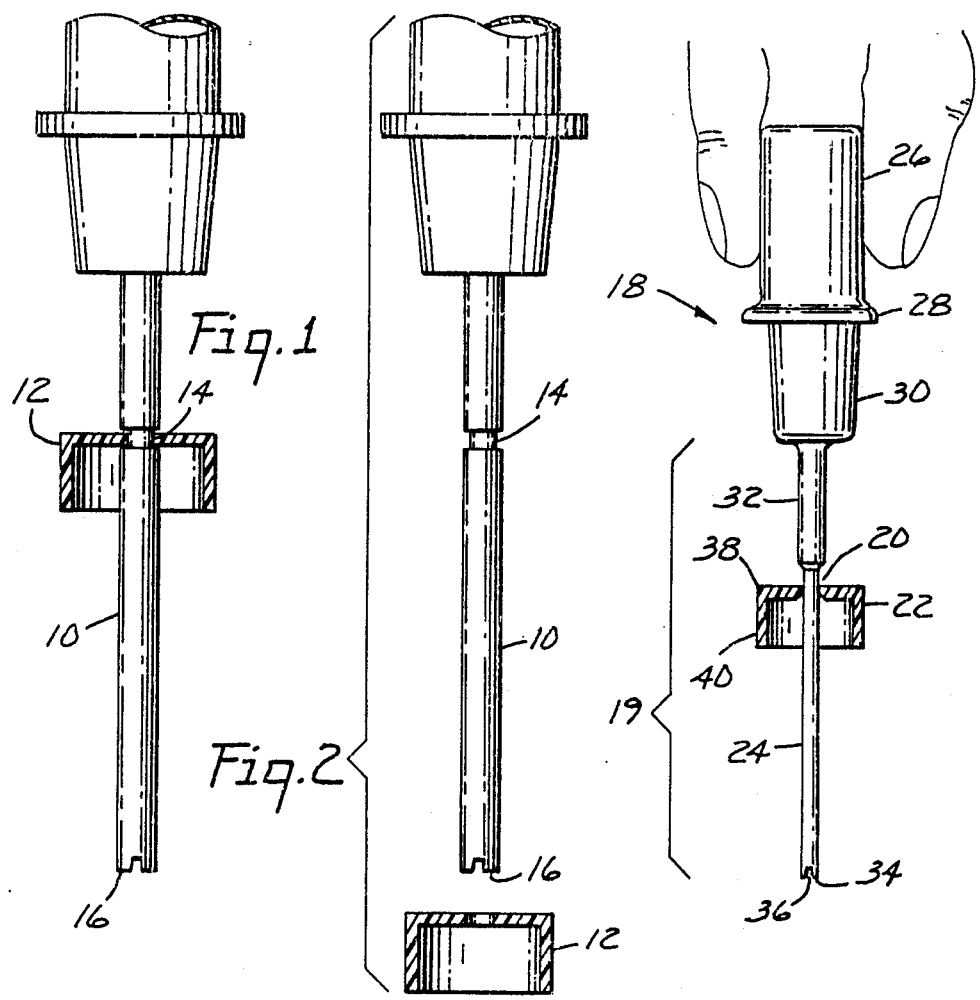
FIG. 1 illustrates an embodiment of a wand assembly of the present invention wherein the elongate rod and collar are molded as separate parts and the collar is shown attached to the rod by releasably attaching the collar in a recessed groove in the rod.
FIG. 2 illustrates the embodiment of FIG. 1 wherein the collar is shown after is has been displaced from the groove and removed from the rod over the tip portion of the rod.
FIG. 3 illustrates a preferred wand of the present invention, wherein the elongate rod and collar are integrally molded of polymeric material and the means for releasably attaching the collar to the rod are provided by a thin layer of the polymeric material.

Wand assemblies were integrally molded, substantially as illustrated in FIG. 3.

A two-plate, steel, single cavity mold was built by machining, having slides to form the center portion. The mold was designed with a core pin that was adjustable in length in order to optimize the thickness of the thin layer of polymeric material. A hypodermic needle having an interior bore of the optimal outside diameter of the tip portion of the rod was inserted into the mold. The part was ejected from the rod end by an ejector pin that fit the internal bore of the hypodermic needle and that had the negative imprint of the groove formed by electrical discharge machining on its material facing end.

Wand assemblies were prepared using the above-described mold on a (reciprocating screw, two-stage screw-type) injection molding machine (3 oz. (maximum plastic), 75 ton (clamping capacity)) Van Dorn, Plastic Machinery Co., Strongsville, OH), using polystyrene ("KR03 K-Resin" (dried), Phillips 66 Company, Pasadena, TX).

The wand assemblies were molded at a cycle time of 15 seconds, mold temperature of 32° C. (90° F.), material temperature of 216° C. (420° F.) and a molding pressure of 562 kg/cm$^2$ (8,000 psi).

EXAMPLE 2

Reproducibility and Accuracy

The reproducibility and accuracy of wand assemblies prepared as described in EXAMPLE 1 were compared to that of wand assemblies with their collars already (i.e., prematurely) removed. The wand assemblies were designed to be capable of picking up $10^7$ bacteria. The wand assemblies were used in the identical manner to pick up colonies of the indicated bacteria, and the collars, of those wand assemblies still having collars, were removed to wipe the peripheral surface of the rods. The wands were then transfered to bottles containing buffered solution and the bacteria were dislodged by shaking. Dilutions were plated out and the quantity of bacteria originally picked up by each wand assembly was calculated based on the dilutions made. The results are set forth below in TABLE A.

TABLE A

| Organism | Colony Forming Units (CFU × $10^7$) | |
|---|---|---|
|  | (No collar) | (Collar) |
| Klebsiella | 2.90, 3.20 | 0.75, 1.15 |
| E. coli | 2.70, 4.90 | 0.95, 1.15 |
| S. Aureus | 5.80, 10.00 | 2.20, 1.30 |
| P. aeruginosa | 3.00, 1.80 | 0.70, 1.30 |
| S. faecalis | 10.00, 8.00 | 2.05, 2.10 |

As can be seen in TABLE A, wand assemblies having no collar picked up larger, and more variable, quantities of bacteria than were intended (i.e., $1.0 \times 10^7$ CFU). Wand assemblies having collars according to the present invention picked up smaller quantities, that were both closer to the intended quantities and less variable. It is expected that the ability to routinely pick up within one-half log of the intended, i.e., predetermined, quantity (in this case from 0.3 to $3.0 \times 10^7$ CFU) will generally be sufficient for commercial purposes. The wand assembly of the present invention was therefore more accurate (i.e., closer to the expected values) and more precise (i.e., values closer to each other) than was the rod without a collar, and resulted in values that fell within the limits of commercial desirability.

We claim:

1. A wand assembly for picking up a predetermined quantity of bacteria from at least one growth colony of the bacteria, said assembly comprising:

an elongate rod having an axis, opposite upper and lower ends, an upper portion adjacent said upper end adapted for manual engagement, an elongate tip portion adjacent said lower end, said tip portion having a peripheral surface and a generally uniform cross sectional shape along said axis, said tip portion having a groove opening through said lower end with said groove having a size adapted to ingest the predetermined quantity of bacteria by capillary action;

a collar around said rod, said collar comprising a wiping portion adapted to move axially in close proximity along said peripheral surface of said tip portion to wipe unwanted bacteria from said peripheral surface; and means for releasably attaching said collar to said rod at a predetermined axial distance from said lower end with said wiping portion adjacent said peripheral surface.

2. A wand assembly according to claim 1 wherein said wand assembly is integrally molded of polymeric material and said means for releasably attaching is a thin layer of said polymeric material joining said wiping portion to said rod, said thin layer being adapted to be broken upon application of a moderate force to move said collar axially along said tip portion toward said lower end.

3. A wand assembly according to claim 1 wherein said rod has a groove recessed from said peripheral surface at said predetermined axial distance from said lower end, and said wiping portion of said collar has an inner surface defining a central opening in said wiping portion having a smaller cross sectional area than the cross sectional area of said tip portion, a part of said wiping portion adjacent said inner surface being positioned in said groove to provide said means for releasably attaching, said wiping portion being sufficiently flexible to be displaced from said groove and slid along said tip portion upon application of a moderate force to move said collar axially along said tip portion toward said lower end.

4. A wand assembly according to claim 1 wherein said predetermined distance is at least 2.54 centimeters.

5. A wand assembly according to claim 1 wherein said tip portion is cylindrical and has a diameter of about 0.082 centimeter.

6. A wand assembly according to claim 2 wherein said polymeric material is polystyrene.

7. A wand assembly according to claim 1 wherein said wiping portion extends generally radially of said rod and has an outer periphery, and said collar further includes a generally cylindrical flange portion coaxial with and spaced from said rod, said flange portion having an end attached to the outer periphery of said wiping portion and an opposite end projecting toward said lower end, said wiping portion and flange defining a barrier adapted to protect a user's fingers from contact with said lower end portion.

8. A wand assembly according to claim 1 wherein said upper portion has a substantially larger diameter than said tip portion, and said rod further includes a frusto conical portion between said upper portion and tip portion adapted to engage the neck of a bottle.

* * * * *